(12) United States Patent
Mansourian

(10) Patent No.: US 12,390,033 B2
(45) Date of Patent: Aug. 19, 2025

(54) SNORE PREVENTION PILLOW

(71) Applicant: Gretchen Mansourian, Brentwood, TN (US)

(72) Inventor: Gretchen Mansourian, Brentwood, TN (US)

(*) Notice: Subject to any disclaimer, the term of this patent is extended or adjusted under 35 U.S.C. 154(b) by 420 days.

(21) Appl. No.: 18/095,589

(22) Filed: Jan. 11, 2023

(65) Prior Publication Data

US 2024/0225324 A1 Jul. 11, 2024

(51) Int. Cl.
*A61F 5/56* (2006.01)
*A47G 9/10* (2006.01)

(52) U.S. Cl.
CPC .............. *A47G 9/1081* (2013.01); *A61F 5/56* (2013.01); *A47G 2009/1018* (2013.01)

(58) Field of Classification Search
CPC ........ A61F 5/56; A61F 5/055; A61F 5/05891; A61F 5/05883; A61F 5/3707; A47G 9/1081; A47G 2009/1018; A47G 9/10; A47G 9/109; A61G 7/072; A61G 5/121; A61G 7/1084; A61G 13/121; A47C 7/383; A47C 16/00; A47C 7/38; A47C 7/386
See application file for complete search history.

(56) References Cited

U.S. PATENT DOCUMENTS

| | | | |
|---|---|---|---|
| 4,366,815 A | 1/1983 | Broomes | |
| 4,966,136 A * | 10/1990 | Bates | A61F 5/3738 602/18 |
| 10,548,405 B2 * | 2/2020 | Komsky | A47C 7/383 |
| 2012/0234330 A1 | 9/2012 | Saiz | |
| 2014/0082845 A1 * | 3/2014 | Pastrmac | A47G 9/1081 5/636 |
| 2017/0065108 A1 * | 3/2017 | Thorn | A47G 9/1027 |
| 2017/0239076 A1 | 8/2017 | Stanton | |
| 2018/0055675 A1 * | 3/2018 | Hatto | A61F 5/055 |
| 2018/0243122 A1 * | 8/2018 | DeSantis | A61F 5/055 |
| 2021/0037985 A1 | 2/2021 | Wu | |
| 2021/0337970 A1 * | 11/2021 | Fan | A47G 9/1081 |

FOREIGN PATENT DOCUMENTS

| | | | |
|---|---|---|---|
| EP | 2244675 | 11/2010 | |
| EP | 2709569 B1 * | 5/2015 | A61F 5/055 |

OTHER PUBLICATIONS

Dictionary.com, "cushion," https://www.dictionary.com/browse/cushion.*

* cited by examiner

*Primary Examiner* — Victoria Hicks Fisher

(57) ABSTRACT

A chin support assembly for supporting a user's chin to prevent snoring includes a cushion with a first end and a second end. The cushion also has a first lateral side and a second lateral side which each extend between the first end and the second end. The cushion is bendable to be positioned in a use configuration in which the first end and the second end face a same direction. A first strap is connected to the first end and a second strap is connected to the second end. Each of the first strap and the second strap are shaped to extend around and engage a neck of a user.

18 Claims, 7 Drawing Sheets

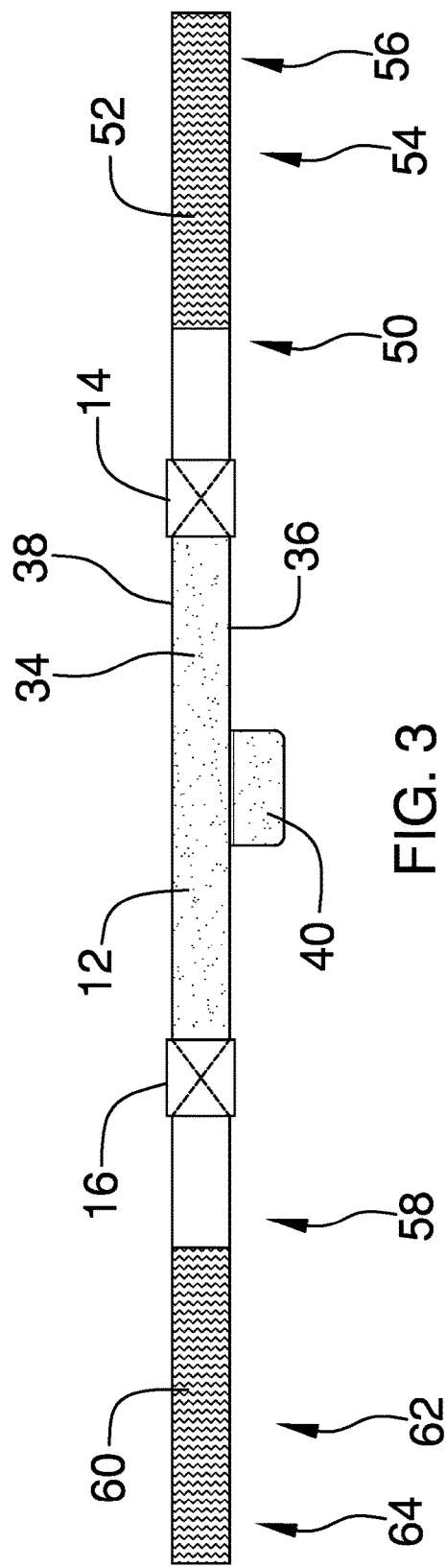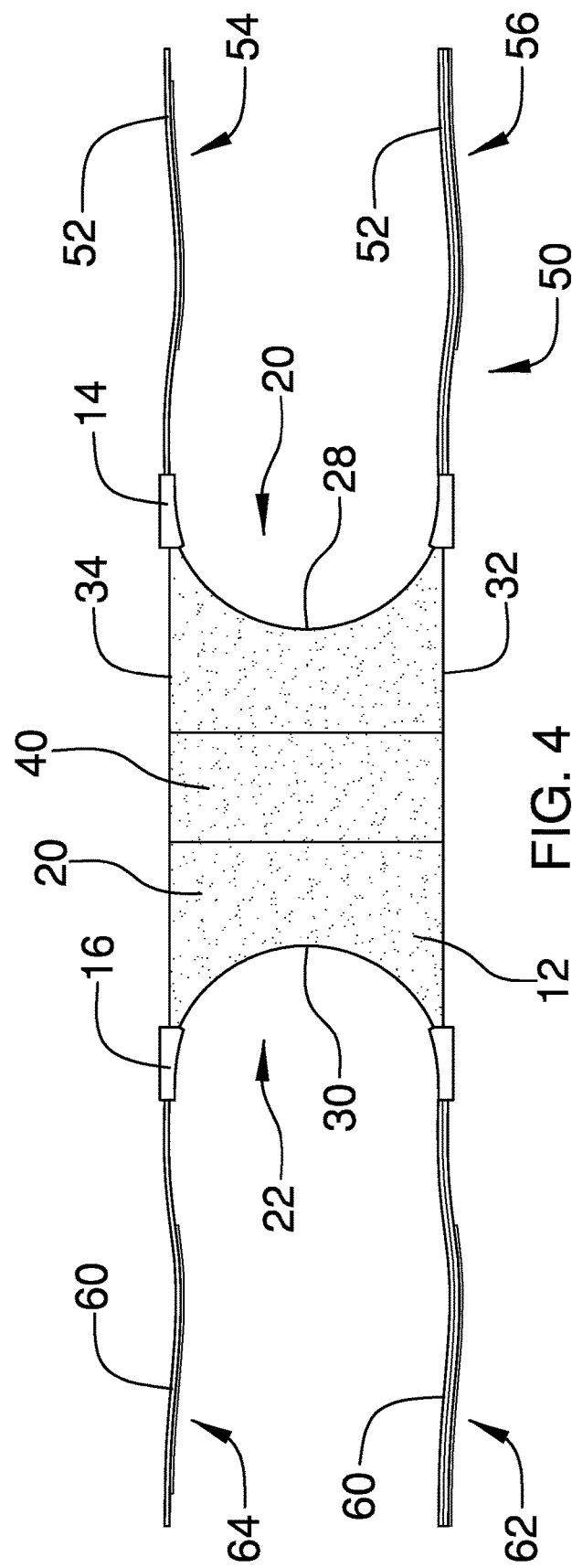

SNORE PREVENTION PILLOW

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention

The disclosure relates to chin support apparatuses and more particularly pertains to a new chin support apparatus for supporting a user's chin to prevent snoring.

(2) Description of Related Art Including Information Disclosed Under 37 CFR 1.97 and 1.98

The prior art relates to chin support apparatuses which wrap around a user's neck to support the chin. Some of these apparatuses utilize resiliently compressible materials such as polymer foams or metal compression springs. However, the prior art does not disclose an apparatus with a cushion that is bendable such that a first end and a second end of the cushion face a same direction and which has straps attached to the first end and the second end for engaging the user's neck.

BRIEF SUMMARY OF THE INVENTION

An embodiment of the disclosure meets the needs presented above by generally comprising a cushion with a first end and a second end. The cushion has a first lateral side and a second lateral side which each extend between the first end and the second end. The cushion has a top surface and a bottom surface which each extend between the first end and the second end and between the first lateral side and the second lateral side. The cushion is positionable in a use configuration wherein the first end and the second end face a same direction. The cushion comprises a resiliently bendable material such that the cushion is bendable into the use configuration. A first strap is coupled to the first end of the cushion. The first strap extends from a first lateral side of the cushion to a second lateral side of the cushion and is configured for engaging the neck of the user. A second strap is coupled to the second end of the cushion. The second strap extends from the second lateral side to the second lateral side of the cushion and is configured for engaging the neck of the user.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 3 is a side view of a cushion according to an embodiment of the disclosure.

FIG. 4 is a top view of a cushion according to an embodiment of the disclosure.

DETAILED DESCRIPTION OF THE INVENTION

Figure 1:
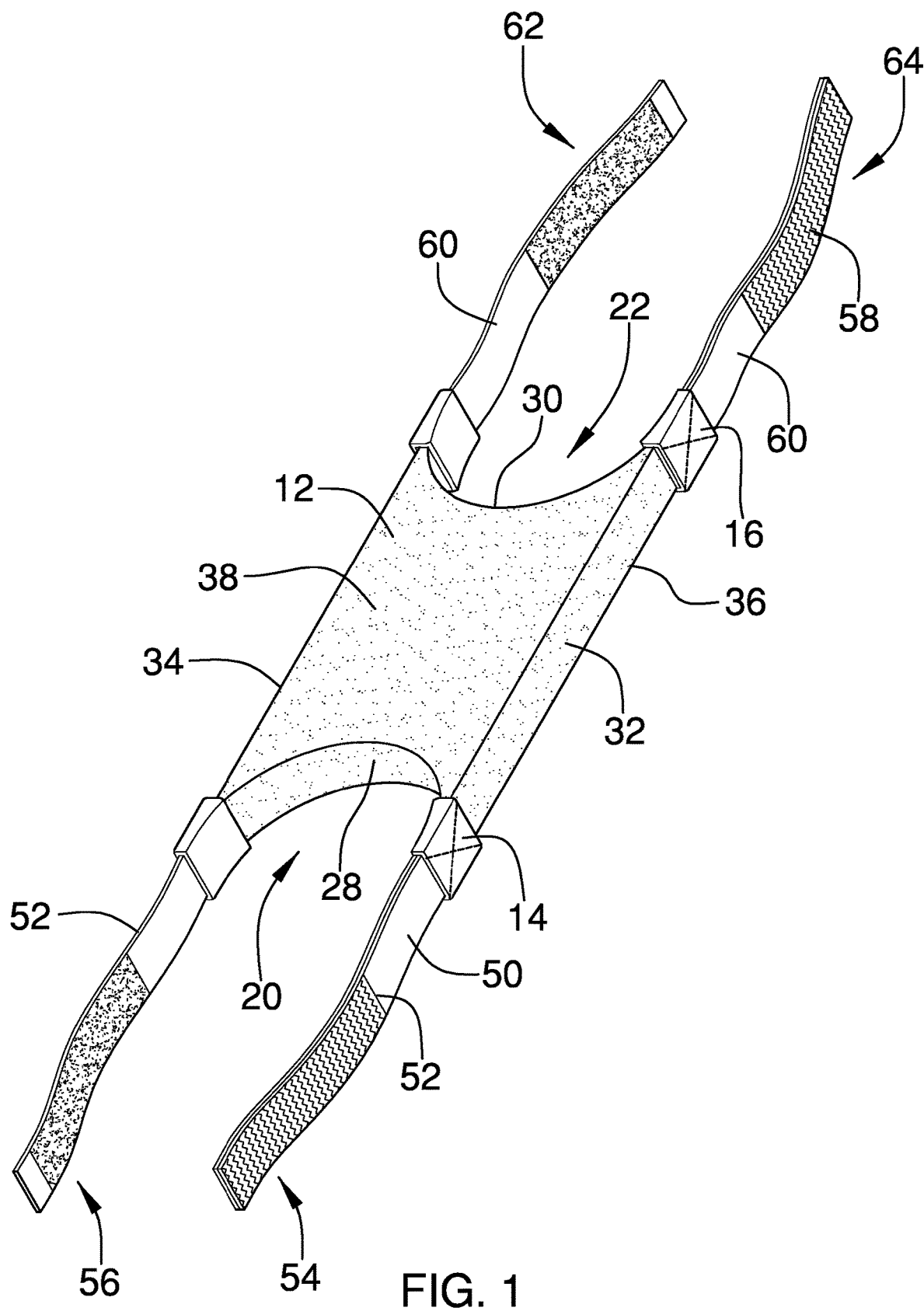
FIG. 1 is a bottom front side perspective view of a cushion of a chin support assembly according to an embodiment of the disclosure.
Figure 2:
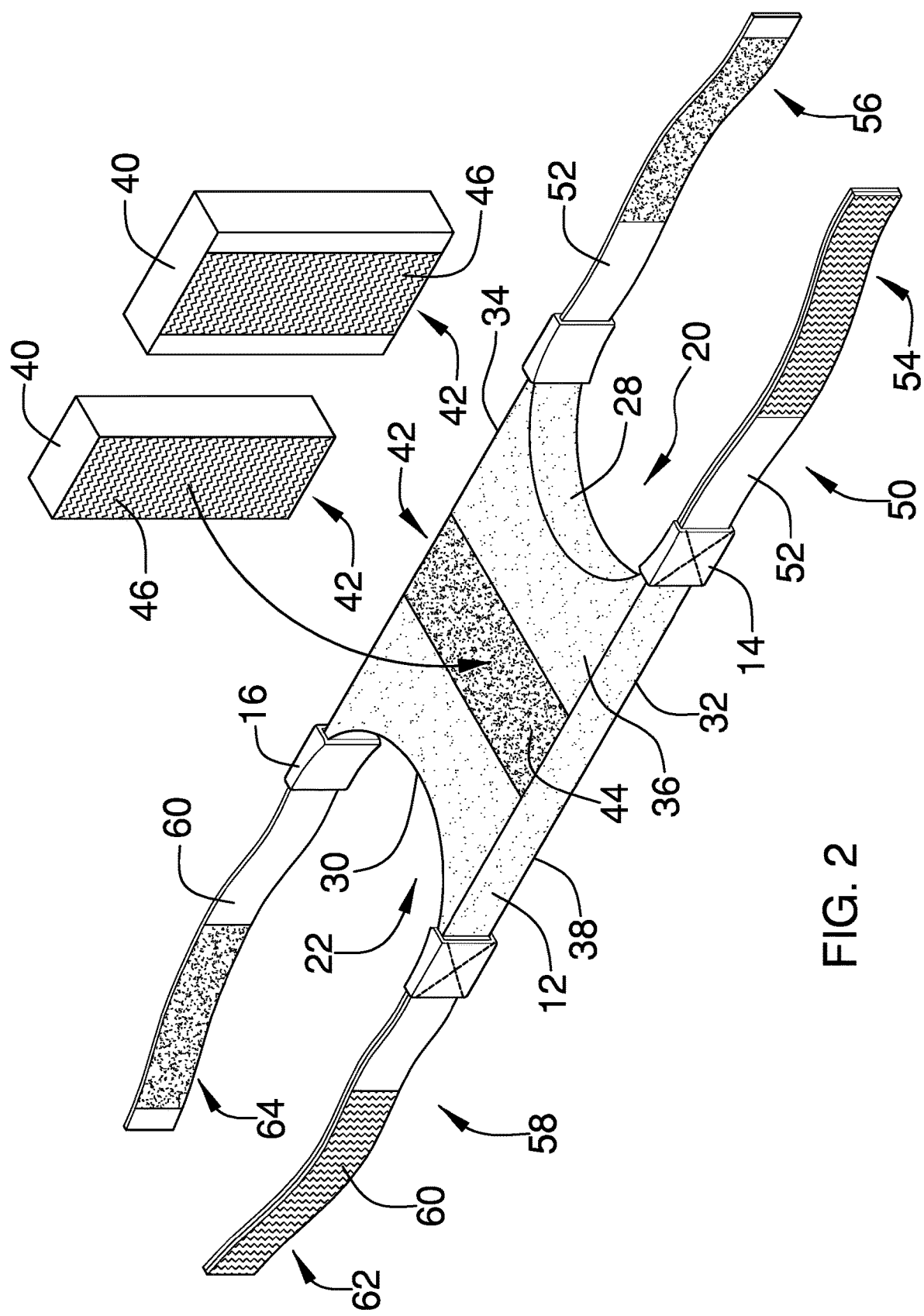
FIG. 2 is a top front side perspective view of a cushion according to an embodiment of the disclosure.
Figure 5:
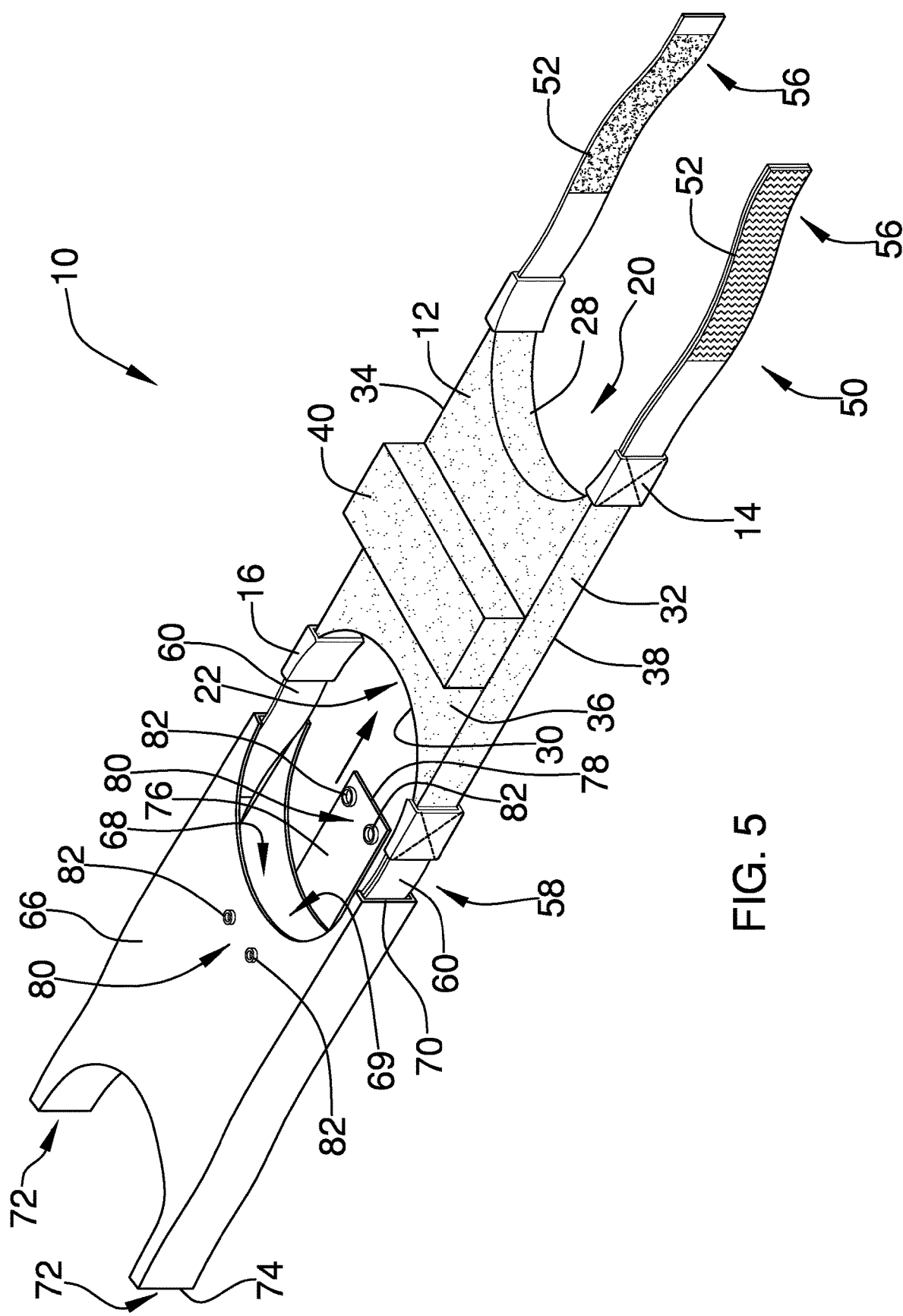
FIG. 5 is an exploded perspective view of an embodiment of the disclosure.
Figure 6:
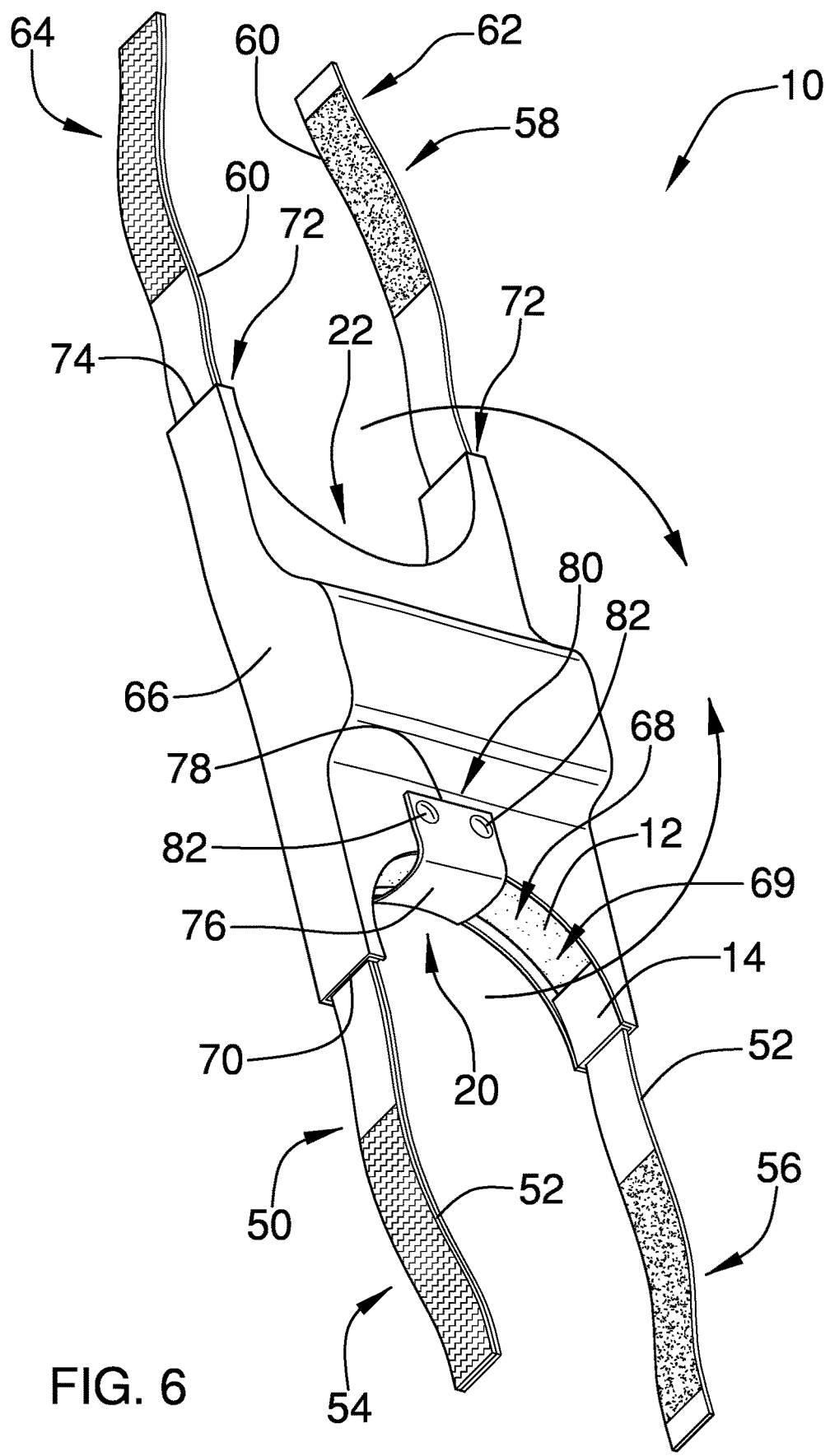
FIG. 6 is a perspective view of an embodiment of the disclosure.
Figure 7:
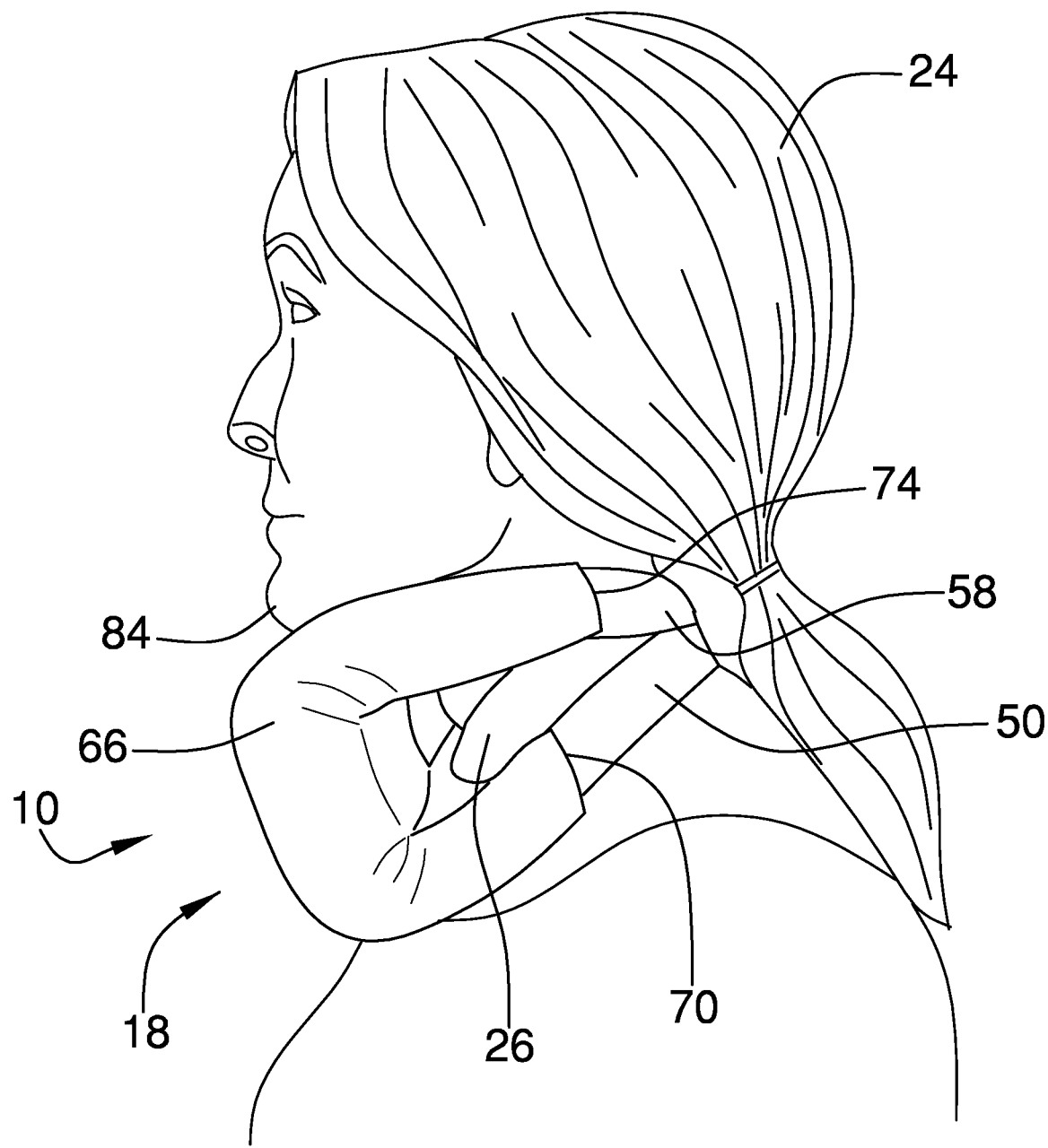
FIG. 7 is a side in-use view of an embodiment of the disclosure.
Figure 8:
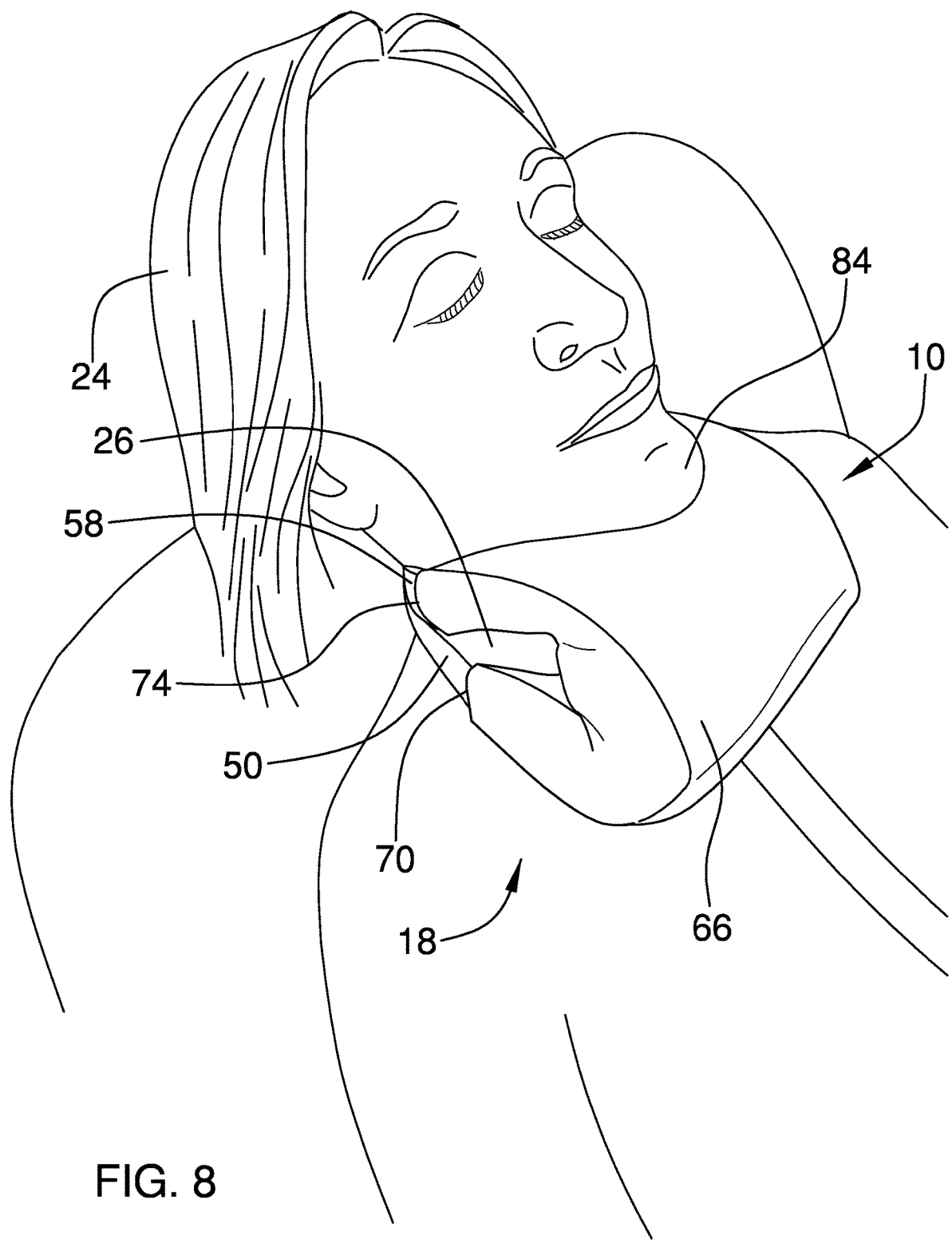
FIG. 8 is a perspective in-use view of an embodiment of the disclosure.

With reference now to the drawings, and in particular to FIGS. 1 through 8 thereof, a new chin support apparatus embodying the principles and concepts of an embodiment of the disclosure and generally designated by the reference numeral 10 will be described.

As best illustrated in FIGS. 1 through 8, the chin support assembly 10 generally comprises a cushion 12 having a first end 14 and a second end 16. The cushion 12 is positionable in a use configuration 18 in which the first end 14 and the second end 16 face a same direction. The cushion 12 comprises a resiliently bendable material such that the cushion 12 is bendable into the use configuration 18. The resiliently bendable material comprises polyester foam but may comprise an alternative plastic foam, elastomer foam, cotton, down, or the like. The cushion 12 has a first recess 20 extending through the first end 14 and a second recess 22 extending through the second end 16. Each of the first recess 20 and the second recess 22 is configured for receiving a neck 26 of a user 24. The first recess 20 defines a first concave surface 28 at the first end 14 of the cushion 12 with a radius of between 2.0 inches and 3.0 inches. The second recess 22 defines a second concave surface 30 at the second end 16 of the cushion 12 which also has a radius of between 2.0 inches and 3.0 inches. A length between the first end 14 and the second end 16 is between 9.0 inches and 13.0 inches. The cushion 12 has a first lateral side 32 and a second lateral side 34 each extending between the first end 14 and the second end 16. A width between the first lateral side 32 and the second lateral side 34 is between 4.0 inches and 6.5 inches. The cushion 12 has a top surface 36 and a bottom surface 38 which each extend between the first end 14 and the second end 16 and extend between the first lateral side 32 and the second lateral side 34. A thickness between the top surface 36 and the bottom surface 38 is between 0.75 inches and 1.25 inches.

Each support block 40 of a pair of support blocks 40 is interchangeably mountable to the top surface 36 of the cushion 12. The cushion 12 bends around a selected support block 40 of the pair of support blocks 40 when the selected support block 40 is mounted to the top surface 36 and the cushion 12 is positioned in the use configuration 18. A width of the selected support block 40 extends between the first end 14 and the second end 16 of the cushion 12 when the selected support block 40 is mounted to the top surface 36. The size of the width of each support block 40 of the pair of support blocks 40 is different from each other. In one embodiment, the pair of support blocks 40 includes a first support block 40 and a second support block 40 such that the width of the first support block 40 is between 1.5 inches and 2.5 inches and the width of the second support block 40 is between 2.5 inches and 3.5 inches. Each support block 40 of the pair of support blocks 40 extends between 0.75 inches and 1.25 inches away from the top surface 36 when mounted to the top surface 36. Each support block 40 of the pair of support blocks 40 also fully extends between the first lateral side 32 and the second lateral side 34 of the cushion 12 when mounted to the top surface 36.

A block fastener 42 is coupled to the cushion 12 and each support block 40 of the pair of support blocks 40. The block fastener 42 comprises a first mating member 44 and a second mating member 46, the second mating member 46 being matable with the first mating member 44. The first mating member 44 is coupled to the top surface 36 of the cushion 12, and the second mating member 46 is coupled to each support block 40 of the pair of support blocks 40. The block fastener 42 comprises a hook-and-loop fastener 48 but may comprise a snap fastener, latch, button, zipper, or the like.

A first strap 50 is coupled to the first end 14 of the cushion 12. The first strap 50 extends from the first lateral side 32 to the second lateral side 34 of the cushion 12 and is configured for engaging the neck 26 of the user 24. The first strap 50 comprises a pair of first strap segments 52, each of which is releasably attachable to each other via a first strap connector 54. The first strap connector 54 is coupled to each first strap segment 52 of the pair of first strap segments 52. The first strap connector 54 comprises a hook-and-loop fastener 56, but may comprise a snap fastener, buckle, zipper, button, or the like.

A second strap 58 is coupled to the second end 16 of the cushion 12. The second strap 58 extends from the first lateral side 32 to the second lateral side 34 of the cushion 12 and is configured for engaging the neck 26 of the user 24. The second strap 58 comprises a pair of second strap segments 60, each of which is releasably attachable to each other via a second strap connector 62. The second strap connector 62 is coupled to each second strap segment 60 of the pair of second strap segments 60. The second strap connector 62 comprises a hook-and-loop fastener 64, but may comprise a snap fastener, buckle, zipper, button, or the like.

A cover 66 is provided for removably encasing the cushion 12 and the selected support block 40. The cushion 12 and the selected support block 40 are positioned within an interior space 68 of the cover 66, and each of the first strap 50 and the second strap 58 extend outwardly away from the cover 66. The cover 66 conforms to the cushion 12 and the selected support block 40. The cover 66 has an opening 69 extending through a front end 70 of the cover 66 for receiving each of the cushion 12, the selected support block 40, and the second strap 58. The first strap 50 extends away from the opening 69. The cover 66 also has a pair of apertures 72, each of which extends through a back end 74 of the cover 66 for receiving each second strap segment 60 of the pair of second strap segments 60. Each second strap segment 60 of the pair of second strap segments 60 extend away from the back end 74 of the cover 66. The cover 66 is constructed of a soft material for non-abrasively engaging the skin of the user 24. The cover 66 is also washable with water and a detergent. The cover 66 may be constructed of cotton, polyester, nylon, or the like.

A retainer 76 is coupled to the cover 66 for retaining the cushion 12 within the interior space 68. The retainer 76 is coupled to the cover 66 adjacent to the first end 14 of the cover 66 and has a free end 78 which is removably attached to the cover 66 such that the retainer 76 crosses the opening 69 and retains the cushion 12 within the interior space 68. A retainer fastener 80 is coupled to the free end 78 of the retainer 76 and the cover 66 for releasably attaching the free end 78 to the cover 66. The retainer fastener 80 comprises a pair of snap fasteners 82 but may comprise a hook-and-loop fastener, a button, a zipper, or the like.

In use, one of the pair of support blocks 40 is selected and mounted to the top surface 36 of the cushion 12. The cover 66 is added which conforms to the cushion 12 and the selected support block 40. The cushion 12 is positioned into the use configuration 18 and positioned underneath a chin 84 of the user 24. The first strap 50 and the second strap 58 are positioned in engagement with the neck 26 of the user 24 such that the chin support assembly 10 is secured to the neck 26 of the user 24.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A chin support assembly for preventing snoring, the chin support assembly comprising:
   a cushion having a first end and a second end, said cushion having a first lateral side and a second lateral side extending between said first end and said second end, said cushion having a top surface and a bottom surface, each of said top surface and said bottom surface extending between said first end and said second end and extending between said first lateral side and said second lateral side, said cushion being positionable in a use configuration wherein said first end and said second end face a same direction, said cushion comprising a resiliently bendable material such that said cushion is bendable into said use configuration;
   a first strap being coupled to said first end of said cushion, said first strap extending from the first lateral side of said cushion to the second lateral side of said cushion, said first strap being configured for engaging a neck of a user;
   a second strap being coupled to said second end of said cushion, said second strap extending from said first lateral side to said second lateral side of said cushion, said second strap being configured for engaging said neck of said user;
   a pair of support blocks, each support block of said pair of support blocks being interchangeably mountable to said top surface of said cushion, said cushion bending around a selected support block of said pair of support blocks when said selected support block is mounted to said top surface and said cushion is positioned in said use configuration; and
   a cover for removably encasing said cushion and said selected support block, said cover defining an interior space, said cushion and said selected support block being positioned within said interior space, each of said first strap and said second strap extending outwardly away from said cover, said cover conforming to said cushion and said selected support block, said cover having an opening extending through a front end of said cover for receiving each of said cushion, said selected support block, and said second strap, said first strap extending away from said opening, said cover having an aperture extending through a back end of said cover for receiving said second strap, said second strap extending away from said back end of said cover.

2. The chin support assembly of claim 1, wherein said resiliently bendable material comprises polyester foam.

3. The chin support assembly of claim 1, wherein said cushion has a first recess extending through said first end, said cushion having a second recess extending through said second end, each of said first recess and said second recess being configured for receiving the neck of the user.

4. The chin support assembly of claim 3, wherein said first recess defines a first concave surface at said first end of said cushion, a radius of said first concave surface being between 2.0 inches and 3.0 inches, said second recess defining a second concave surface at said second end of said cushion, a radius of said second concave surface being between 2.0 inches and 3.0 inches.

5. The chin support assembly of claim 1, wherein a length between said first end and said second end is between 9.0 inches and 13.0 inches.

6. The chin support assembly of claim 1, wherein a width between said first lateral side and said second lateral side is between 4.0 inches and 6.5 inches.

7. The chin support assembly of claim 1, wherein a thickness between said top surface and said bottom surface is between 0.75 inches and 1.25 inches.

8. The chin support assembly of claim 1, wherein a width of said selected support block extends between said first end and said second end of said cushion when said selected support block is mounted to said top surface, a size of said width of each support block of said pair of support blocks being different from each other.

9. The chin support assembly of claim 8, wherein said pair of support blocks includes a first support block and a second support block, said width of said first support block being between 1.5 inches and 2.5 inches, said width of said second support block being between 2.5 inches and 3.5 inches, each support block of said pair of support blocks extending between 0.75 inches and 1.25 inches away from said top surface when mounted to said top surface.

10. The chin support assembly of claim 8, wherein each support block of said pair of support blocks fully extends between said first lateral side and said second lateral side of said cushion when mounted to said top surface.

11. The chin support assembly of claim 1, further comprising a block fastener being coupled to said cushion and each support block of said pair of support blocks, said block fastener comprising a first mating member and a second mating member, said second mating member being matable with said first mating member, said first mating member being coupled to said top surface of said cushion, said second mating member being coupled to each support block of said pair of support blocks.

12. The chin support assembly of claim 11, wherein said block fastener comprises a hook-and-loop fastener.

13. The chin support assembly of claim 1, wherein said first strap comprises a pair of first strap segments, each first strap segment of said pair of first strap segments being releasably attachable to each other, said second strap comprising a pair of second strap segments, each second strap segment of said pair of second strap segments being releasably attachable to each other.

14. The chin support assembly of claim 13, further comprising:
   a first strap connector being coupled to each first strap segment of said pair of first strap segments; and
   a second strap connector being coupled to each second strap segment of said pair of second strap segments.

15. The chin support assembly of claim 14, said first strap connector comprising a hook-and-loop fastener, said second strap connector comprising a hook-and-loop fastener.

16. The chin support assembly of claim 14, further comprising a cover for removably encasing said cushion, said cover defining an interior space, said cushion being positioned within said interior space, each of said first strap and said second strap extending outwardly away from said cover, said cover conforming to said cushion, said cover having an opening extending through a front end of said cover for receiving each of said cushion and said second strap, said first strap extending away from said opening, said cover having a pair of apertures, each aperture of said pair of apertures extending through a back end of said cover for receiving each second strap segment of said pair of second strap segments, each second strap segment of said pair of second strap segments extending away from said back end of said cover.

17. The chin support assembly of claim 16, further comprising
   a retainer being coupled to said cover for retaining said cushion within said interior space, said retainer being coupled to said cover, said retainer having a free end being removably attached to said cover such that said retainer crosses said opening and retains said cushion within said interior space; and a retainer fastener being coupled to said free end of said retainer and said cover for releasably attaching said free end to said cover, said retainer fastener comprising a pair of snap fasteners.

18. A chin support assembly for preventing snoring, the chin support assembly comprising:

a cushion having a first end and a second end, said cushion being positionable in a use configuration wherein said first end and said second end face a same direction, said cushion comprising a resiliently bendable material such that said cushion is bendable into said use configuration, said resiliently bendable material comprising polyester foam, said cushion having a first recess extending through said first end, said cushion having a second recess extending through said second end, each of said first recess and said second recess being configured for receiving a neck of a user, said first recess defining a first concave surface at said first end of said cushion, a radius of said first concave surface being between 2.0 inches and 3.0 inches, said second recess defining a second concave surface at said second end of said cushion, a radius of said second concave surface being between 2.0 inches and 3.0 inches, a length between said first end and said second end being between 9.0 inches and 13.0 inches, said cushion having a first lateral side and a second lateral side each extending between said first end and said second end, a width between said first lateral side and said second lateral side being between 4.0 inches and 6.5 inches, said cushion having a top surface and a bottom surface, each of said top surface and said bottom surface extending between said first end and said second end and extending between said first lateral side and said second lateral side, a thickness between said top surface and said bottom surface being between 0.75 inches and 1.25 inches;

a pair of support blocks, each support block of said pair of support blocks being interchangeably mountable to said top surface of said cushion, said cushion bending around a selected support block of said pair of support blocks when said selected support block is mounted to said top surface and said cushion is positioned in said use configuration, a width of said selected support block extending between said first end and said second end of said cushion when said selected support block is mounted to said top surface, a size of said width of each support block of said pair of support blocks being different from each other, said pair of support blocks including a first support block and a second support block, said width of said first support block being between 1.5 inches and 2.5 inches, said width of said second support block being between 2.5 inches and 3.5 inches, each support block of said pair of support blocks extending between 0.75 inches and 1.25 inches away from said top surface when mounted to said top surface, each support block of said pair of support blocks fully extending between said first lateral side and said second lateral side of said cushion when mounted to said top surface;

a block fastener being coupled to said cushion and each support block of said pair of support blocks, said block fastener comprising a first mating member and a second mating member, said second mating member being matable with said first mating member, said first mating member being coupled to said top surface of said cushion, said second mating member being coupled to each support block of said pair of support blocks, said block fastener comprising a hook-and-loop fastener;

a first strap being coupled to said first end of said cushion, said first strap extending from said first lateral side to said second lateral side of said cushion, said first strap being configured for engaging said neck of said user, said first strap comprising a pair of first strap segments, each first strap segment of said pair of first strap segments, being releasably attachable to each other;

a first strap connector being coupled to each first strap segment of said pair of first strap segments, said first strap connector comprising a hook-and-loop fastener;

a second strap being coupled to said second end of said cushion, said second strap extending from said first lateral side to said second lateral side of said cushion, said second strap being configured for engaging said neck of said user, said second strap comprising a pair of second strap segments, each second strap segment of said pair of second strap segments being releasably attachable to each other;

a second strap connector being coupled to each second strap segment of said pair of second strap segments, said second strap connector comprising a hook-and-loop fastener;

a cover for removably encasing said cushion and said selected support block, said cover defining an interior space, said cushion and said selected support block being positioned within said interior space, each of said first strap and said second strap extending outwardly away from said cover, said cover conforming to said cushion and said selected support block, said cover having an opening extending through a front end of said cover for receiving each of said cushion, said selected support block, and said second strap, said first strap extending away from said opening, said cover having a pair of apertures, each aperture of said pair of apertures extending through a back end of said cover for receiving each second strap segment of said pair of second strap segments, each second strap segment of said pair of second strap segments extending away from said back end of said cover;

a retainer being coupled to said cover for retaining said cushion within said interior space, said retainer being coupled to said cover, said retainer having a free end being removably attached to said cover such that said retainer crosses said opening and retains said cushion within said interior space; and a retainer fastener being coupled to said free end of said retainer and said cover for releasably attaching said free end to said cover, said retainer fastener comprising a pair of snap fasteners.

* * * * *